United States Patent
Murray et al.

[11] Patent Number: 5,324,265
[45] Date of Patent: Jun. 28, 1994

[54] HYPODERMIC SAFETY SYRINGE WITH RETRACTING NEEDLE SYSTEM

[75] Inventors: Kenneth W. Murray, Littleton, Colo.; Charles C. Gabbard; Nola M. H. Gabbard, both of Mt. Juliet, Tenn.

[73] Assignee: Gabbard Murray Gabbard Inc., Mt. Juliet, Tenn.

[21] Appl. No.: 139,467

[22] Filed: Oct. 20, 1993

[51] Int. Cl.$^5$ ............................................. A61M 5/32
[52] U.S. Cl. .................................... 604/110; 604/195
[58] Field of Search ............... 604/110, 192, 187, 198, 604/263, 195

[56] References Cited

U.S. PATENT DOCUMENTS

| | | | |
|---|---|---|---|
| 4,838,869 | 6/1989 | Allard | 604/110 |
| 4,874,382 | 10/1989 | Lindemann et al. | 604/195 |
| 4,955,870 | 9/1990 | Ridderheim et al. | 604/110 X |
| 5,211,628 | 5/1993 | Marshall | 604/110 |

Primary Examiner—John D. Yasko

[57] ABSTRACT

A hypodermic safety syringe, according to the present invention, includes a barrel having an open end, a cone shaped end and an interior surface. A hollow needle and carriage assembly is temporarily attached and is restrained by four catches extending from the interior tapered surface. A plunger assembly is reciprocally received into the barrel and is in air-tight engagement with the interior surface of the barrel. Thus, an interior chamber is formed in the barrel whereby liquids are retreived and emmited through the hollow needle. A cavity within the plunger contains a spring and retraction guide assembly with a mating member corresponding to mating members extending from the needle carriage. As the mating members contact and become captured the needle and carriage assembly is released by the approaching plunger assembly as the catches are deflected outward by the angled surface of the plunger. At the end of the injection stroke small spherical bearings, in locking contact with the retraction guide, are caused to move outward and into a radially concave interior surface releasing the retraction guide, captured needle and carriage assembly thereby retracted into the cavity within the plunger structure. Thus rendering the syringe safe for handling and transport to disposal.

15 Claims, 5 Drawing Sheets

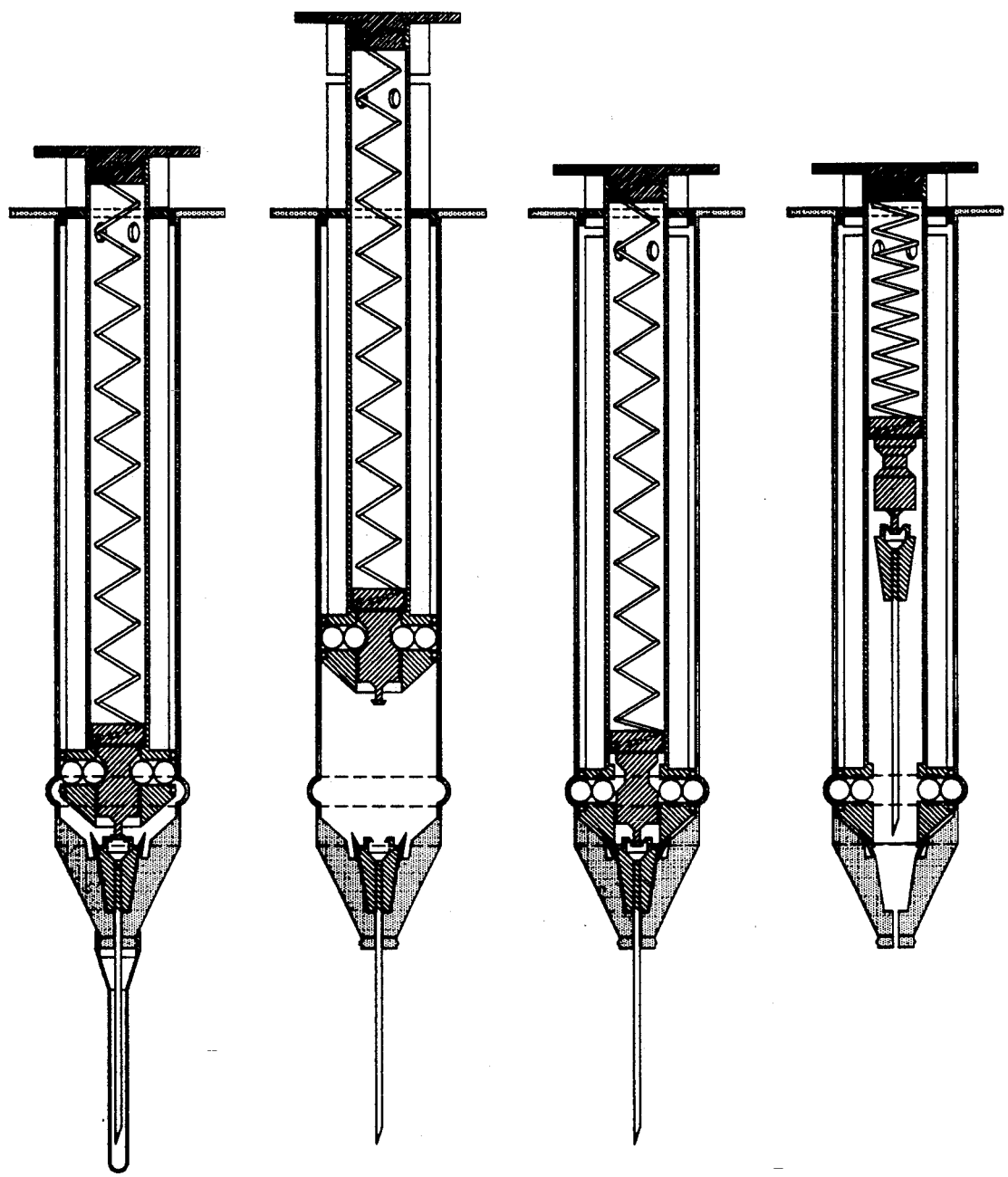

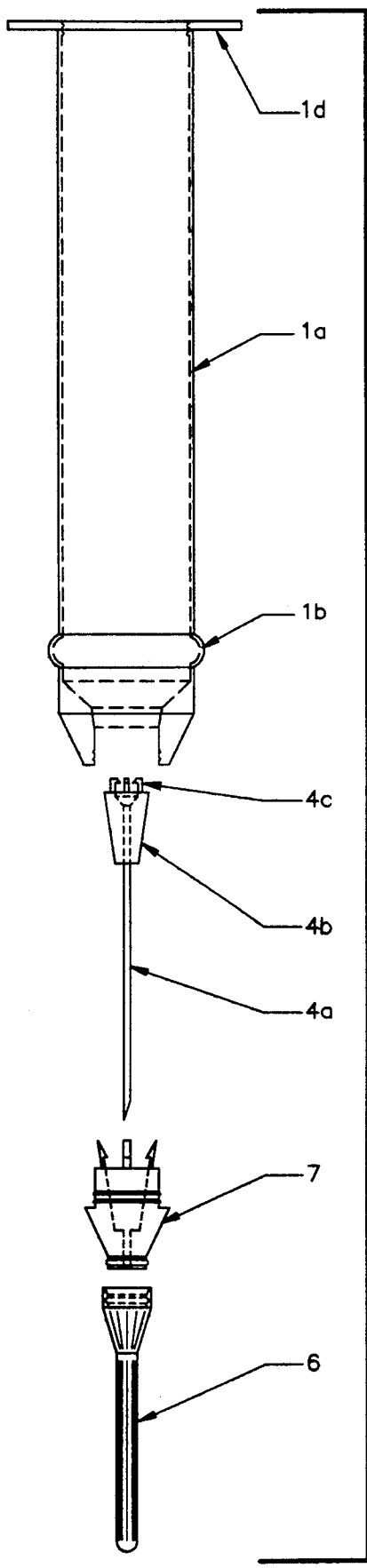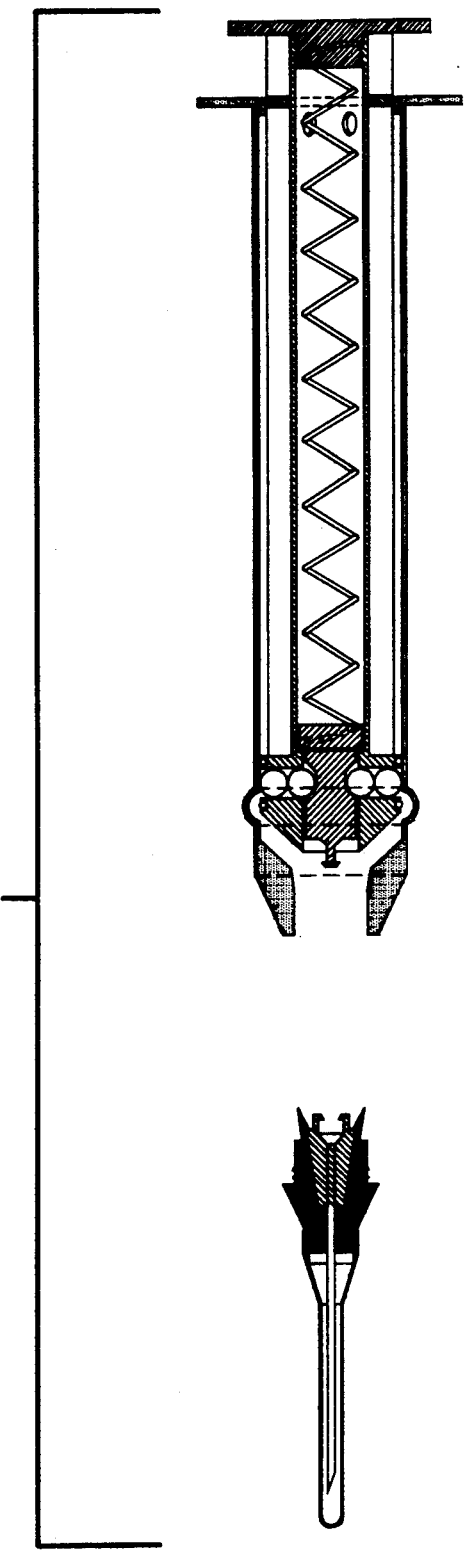
FIG. 13
FIG. 14

HYPODERMIC SAFETY SYRINGE WITH RETRACTING NEEDLE SYSTEM

BACKGROUND OF THE INVENTION

This invention relates to medical and industrial devices used for administering or receiving fluids to or from a patient, area or process and more specifically to a hypodermic syringe with a mechanical system for automatically retracting the needle into the syringe, thereby rendering the syringe useless and safe for handling and transport to disposal.

Current designs for monouse syringes do not allow for the inadvertent or accidental puncture of health care, laboratory and industrial users who come in contact with an exposed needle. Monouse syringes can be used as many times as desired despite labeling and warnings to the contrary. Furthermore, current patented designs for retractable needle type syringes are at best poor in their solutions to the problem of conveying or retracting the needle from the operational condition to a protected or enclosed condition. Some even fail to address covering the needle prior to use. U.S. Pat. No. 4,838,869 to Allard and U.S. Pat. No. 4,955,870 to Ridderheim et al. disclose a means whereby the needle assembly acting as a piston is retracted aft by a spring under tension into a cylindrical chamber within the structure of the plunger and illustrates no means to prevent the pressurization of air trapped in the chamber by the rapidly retracting needle assembly. Clearly, this would miss a basic mechanical need to provide for venting the cylinder to allow air trapped in the cylinder to escape.

These and other weaknesses in the current art designs coupled with economic considerations for manufacture may not permit a viable solution to be available in the market for some years to come. The incidence of injury to life and health by accidental puncture and cross contamination of persons using, handling, or in close proximity to syringes having exposed contaminated needles is greater now than ever before. The need for a safe, reliable, inexpensive, and manufacturable retracting needle syringe is of significant importance.

SUMMARY OF THE INVENTION

The present invention provides a solution to the above-mentioned needs while overcoming the shortcomings of the prior art by providing a simplified approach to design problems in a syringe with a retractable needle. The retractable needle system in this embodiment uses five moving part assemblies including the plunger movement and provides classic mechanical solutions for the restraining, triggering and retracting operations of the needle. The absence of shearable materials or special minute fabrications provides reliability and economy in the manufacture and use of the syringe.

The hypodermic syringe, according to the present invention, includes a barrel having an open end, a cone shaped end with a small orifice, and an interior surface. The small orifice at the coned end of the barrel is of sufficient interior diameter to allow unrestricted passage of a hollow needle mated into a carriage fitting snugly into a tapered interior surface at the coned end of the barrel. The needle carriage is restrained mechanically by four catches extending from the interior tapered surface at the coned end of the barrel with each having a raised lip extending over the larger end of the tapered needle carriage. A plunger assembly is reciprocally received into the barrel at the open end and is in an air-tight engagement with the interior surface of the barrel. The engagement between the plunger and the barrel allows for axial and radial adjustment of the plunger. Thus, providing a variable cylindrical chamber formed between the inserted end of the plunger and the interior surfaces of the barrel. The chamber receives and emits liquids communicating through a hollow needle by hydraulic action resulting from axial adjustments between the plunger and barrel. The plunger structure includes a concentric cylindrically shaped cavity extending axially from one end to the other, wherein an assembly comprised of a cap, a spring and a retraction guide is received. The cap adapts to the cylindrical cavity in the plunger at the end of the plunger protruding from the barrel and is permanently restrained by radial concavities binding aligned radial convexities extending from the interior surface of the barrel. A biasing means or spring is attached into the surface of the cap extending into the cylindrical cavity at one end and attached to a retraction guide at the other. The retraction guide, with radially concave surfaces, allows spherical bearings present in adjacent latitudinal shafts extending from either interior surface of the barrel to extend into the radially concave surfaces and temporarily lock the retraction guide into a fixed position. The position of the retraction guide at the inserted end of the plunger renders the spring extended and under stress. The retraction guide incorporates a means to capture the needle and carriage assembly using a convex mating member that attaches to adapted mating members protruding from the needle carriage when the plunger approaches the coned end of the barrel.

To begin operation, a protective cover about the needle is removed. The exposed portion of the plunger is rotated in either direction to align the longitudinal ribs of the plunger body with the openings in the insert at the open end of the syringe. The needle is placed into a area or process where a desired volume of available liquid may be withdrawn through the needle and into the cylindrical chamber by adjusting the plunger outward and away from the coned end of the barrel. The needle may then be reinserted into a patient area or process and the collected liquid injected into same by adjusting the plunger into and towards the coned end of the barrel. As the plunger approaches the end of the injection stroke a convex mating member extending from the retraction guide inserts and captures mating members extending from the needle carriage. Substantially toward the end of the injection stroke an angled circular surface at the mating end of the plunger comes in contact with four catches extending from the interior tapered surface at the coned end of the barrel. As the plunger continues, the catches are caused to be deflected outward and away from the centerline of the syringe and raised surfaces previously restraining the needle carriage are cleared. As the injection stroke finalizes, spherical bearings restraining a retraction guide align with a radial concave interior surface allowing force acting on the bearings to cause them to be repositioned outward and away from the centerline of the barrel. Thus, releasing the retraction guide coupled with the needle and carriage for retraction into the cylindrical cavity in the plunger by the biasing means or spring. Accordingly, the contaminated needle is contained within the structure of the syringe and renders the syringe unusable and safe for handling and transport to disposal.

In one embodiment, a hypodermic syringe, as summarized herein, uses a alternate biasing means to retract the retraction guide, captured needle and carriage into the cylindrical cavity. The concentric cylindrical shaped cavity within the structure of the plunger is caused to contain a sufficient vacuum force to retract the retraction guide, captured needle and carriage. Thereby, effectively eliminating a need for a spring mechanism.

In a preferred embodiment, a hypodermic syringe, as summarized herein, incorporates a previously detached portion of the cone shape end of the barrel, effectively creating a bushing. The previously detached portion includes the four latches extending outward from the body of the bushing on the end opposite from the cone shaped end. The needle carriage and protective cover are preassembled about the bushing, creating a needle assembly that may contain a variety of needle lengths, diameters, bores and shapes, thus providing additional flexibility, adaptability, and conformity in the selection and operation of the hypodermic syringe. The commencement of operation for this embodiment is identical to the abovementioned embodiment with the exception that, prior to removal of the protective cover and subsequent operational steps, a needle assembly is selected and inserted into the opened end of the barrel and moved substantially inward until radially concave and convex surfaces become aligned, restraining the needle assembly into an air-tight engagement onto the barrel. The protective cover may now be removed and subsequent operational steps described herein executed.

BRIEF DESCRIPTION OF THE DRAWINGS

The drawings will serve to further clarify the present invention. Referencing the following description of embodiments of this invention taken in conjunction with the accompanying drawings wherein:

FIG. 2 serves as a reference to sections taken radially at locations along the syringe;

FIG. 9 is an axial section through the syringe according to the invention in its initial state as provided by manufacture including a protective cover over a protruding needle and prepared for use;

FIG. 10 is an axial section through the syringe according to the invention showing the syringe of FIG. 9 with the plunger adjusted to an intermediate location away from the coned end of the barrel. FIG. 10 serves to illustrate a hypodermic syringe approximately 25% loaded with liquid;

FIG. 11 is an axial section through the syringe according to the invention showing the syringe of FIG. 9 with the plunger fully inserted, the needle and carriage and retraction guide released. The retraction guide is shown in motion towards the interior of the cylindrical cavity in the plunger structure; and FIG. 12 is an axial section through the syringe according to the invention showing the syringe of FIG. 9 after use with the needle and carriage retracted;

FIG. 13 is an exploded view of the barrel assembly parts in a modified arrangement whereby a portion of the coned end of the barrel is previously detached allowing an additional needle assembly; and FIG. 14 is an axial section through the syringe according to the invention showing the syringe of FIG. 9 incorporating the modification of FIG. 13. FIG. 14 serves to illustrate the syringe in a condition prior to FIG. 9 providing the option of needle selection.

DETAILED DESCRIPTION OF THE INVENTION

Figure 1:
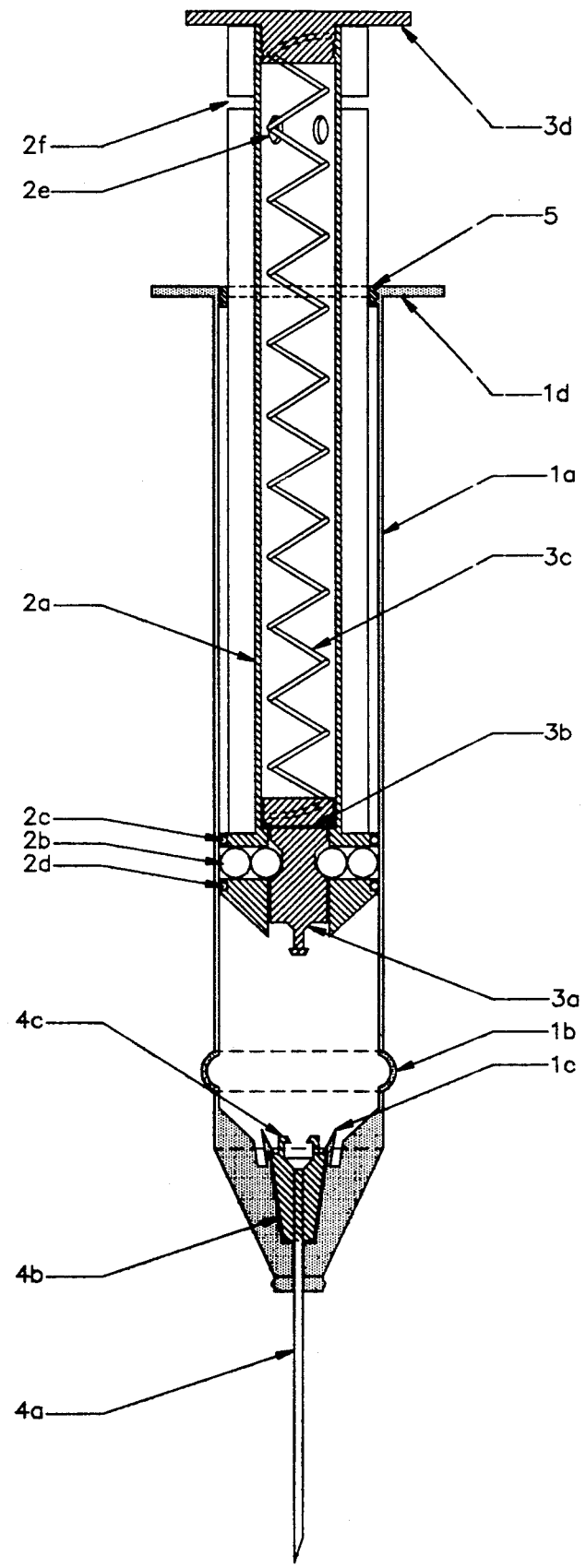
FIG. 1 is an axial section through the syringe according to the present invention with the plunger partially withdrawn and the protective cover about the hollow needle removed for clarity.
Figure 2:
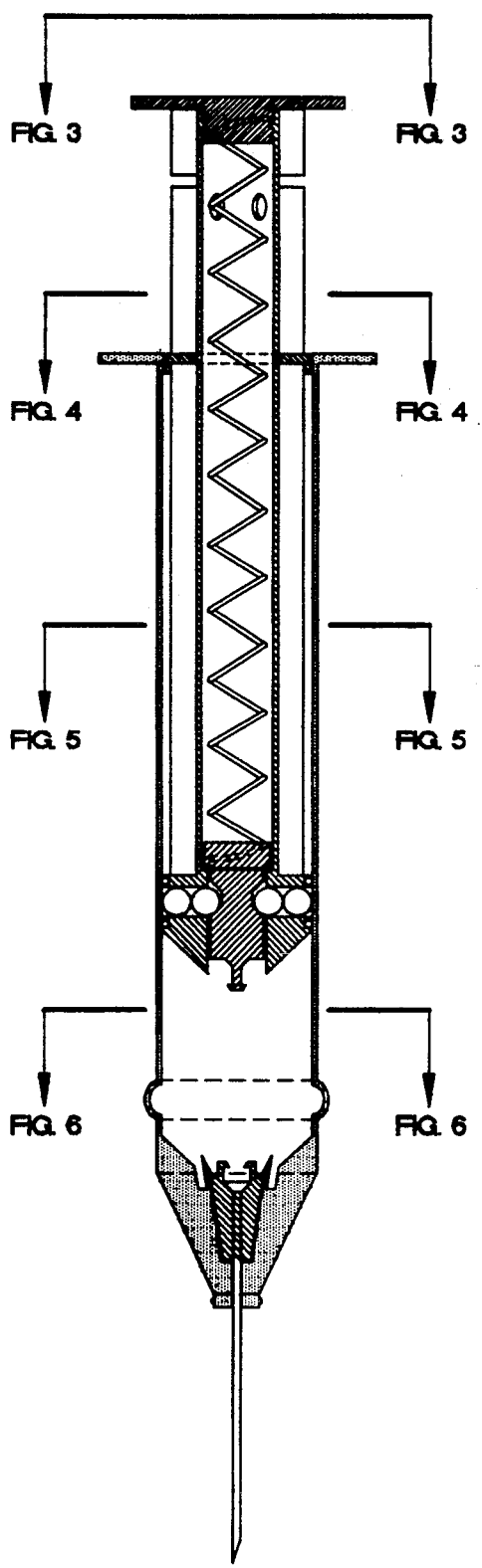
FIG. 2 is an axial section through the syringe provided at a scale that is 81.8416% the size of FIG. 1 and is of identical scale with the remaining figures.
Figure 3:
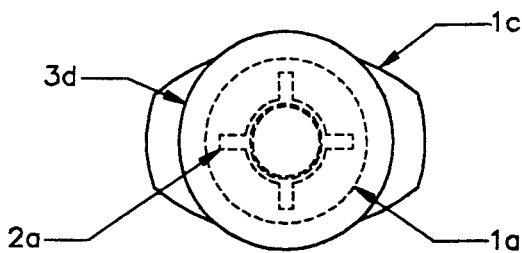
FIG. 3 is a section taken at line FIG.3—FIG.3 of FIG. 2.
Figure 4:
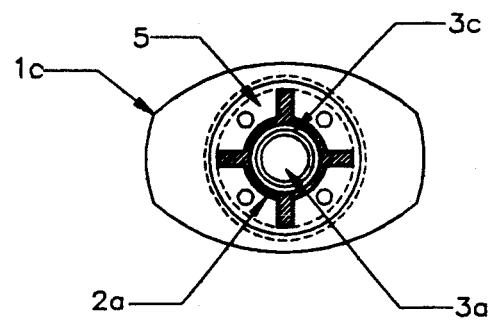
FIG. 4 is a section taken at line FIG.4—FIG.4 of FIG. 2.
Figure 5:
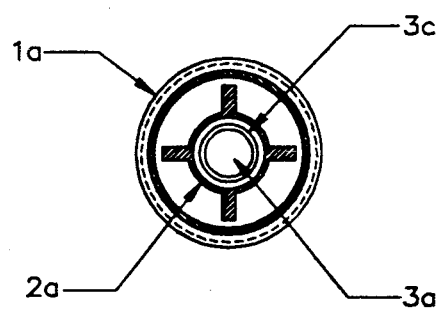
FIG. 5 is a section taken at line FIG.5—FIG.5 of FIG. 2.
Figure 6:
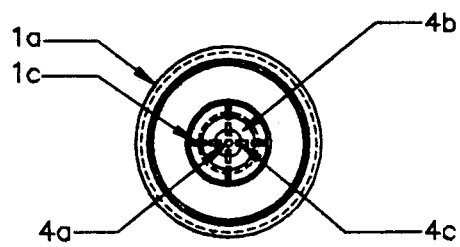
FIG. 6 is a section taken at line FIG.6—FIG.6 of FIG. 2.

As shown in FIGS. 1,3–8 a syringe according to the present invention consists of assemblies, subassemblies and parts wherein numerals and alpha characters are assigned to the various parts, part features and part assemblies for referencing like elements throughout the drawings. Numerals are assigned to a part, similar part and/or part assembly, where alpha characters are significant of sub-parts of assemblies and/or sequencing of part features. The syringe consists of a barrel (1a) having an open end, a coned end with an axial needle receiving bore, and a substantially smooth cylindrically shaped interior surface. A semi-circular grip (1d) an integral part of the barrel (1a) is provided to be gripped with the index and middle fingers of the user while applying pressure to the cap (3d) of the plunger subassembly (3a)–(3d) with the thumb of the same hand during the injection stroke. A radial bulge (1b) provides a concave surface within the interior of the barrel (1a) sized to accept spherical bearings (2b) forced out of latitudinal shafts at the inserted end of the plunger (2a) as it completes the injection stroke. Four radially spaced resilient latches (1c) cause the needle and carriage subassembly (4a)–(4c) to become restrained as raised surfaces of the latches (1c) encroach over the larger end of the needle carriage (4b). A protective cover (6) is placed over the needle and snapped into place using radial concavities and convexities aligned on the interior of the open end of the protective cover (6) and the exterior of the coned end of the barrel (1a) respectively. Thus, the barrel subassembly (1a)–(1d), (4a)–(4c), (6) is prepared to accept the plunger subassembly (2a)–(2f), (3a)–(3d), (5).

Figure 8:
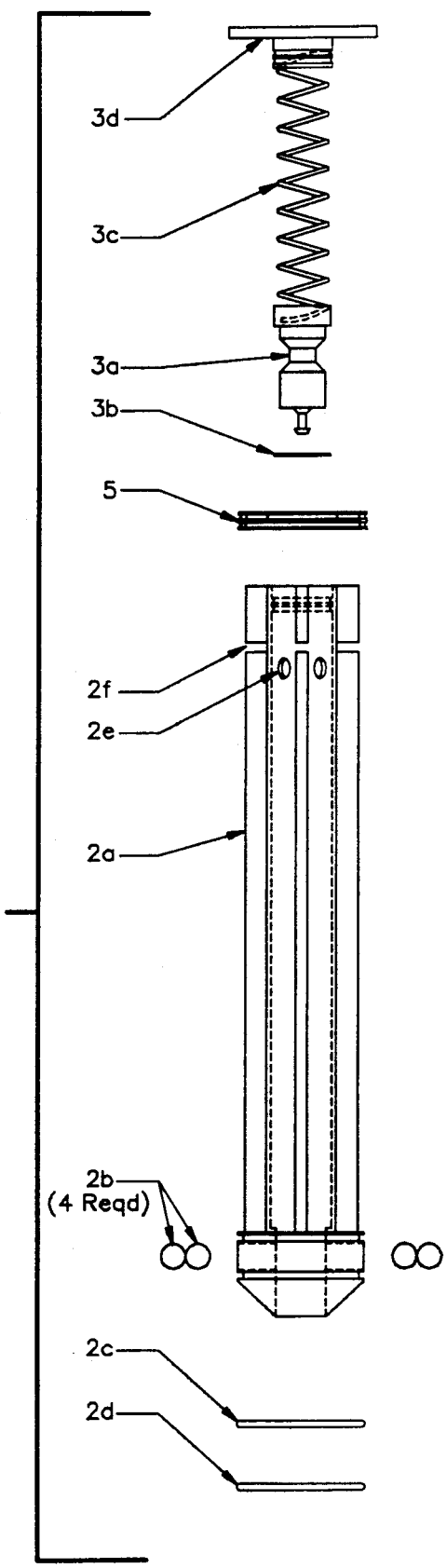
FIG. 8 is an exploded view of the plunger assembly parts in relative positions required for their assembly.

FIG. 8 illustrates the parts incorporated in the plunger subassembly. O-ring seals (2c) and (2d) are placed over the inserted end of the plunger (2a) and into radial concave grooves at the inserted end of the plunger (2a). Four spherical bearings (2b) are inserted into latitudinal shafts extending through the inserted end of the plunger (2a). At the other end of the plunger (2a) an opening in an insert (5), loosely corresponding to the cross sectional geometry of the plunger cavity and ribs (2a), is aligned and passed over the plunger (2a) body to a point aligning with notches (2f) in the ribs of the plunger (2a) structure. The insert (5) is then rotated 45 degrees about the plunger (2a) in either direction, thus locking the insert (5) within the notches (2f). A retraction guide subassembly (3a)-(3d) is fitted with a flat circular seal (3b) over the retraction guide (3a) and snug to a raised circular surface at a point where an integral circular block contains a spring (3c) previously affixed by permanent means. A circular cap (3d) previously affixed to the other end of the spring (3c) by permanent means completes the retraction guide subassembly (3a)-(3d). The retraction guide (3a) end of the retraction guide subassembly (3a)-(3d) is reciprocally received into the concentric circular cavity in the plunger (2a) structure at the end of the plunger (2a) having weep holes (2e), and snapped into place using radial concavities and convexities aligned on the exterior of a raised circular surface containing the spring (3c) of the circular cap (3d) and interior of the weep hole (2e) end of the plunger (2a), respectively. The final preparation of the plunger subassembly (2a)-(2f), (3a)-(3d), (5) requires an external biasing means to transport the retraction guide (3a) towards the insertion end of the plunger to a point where spherical bearings (2b) are moved into locking contact with the radial concave surfaces of the retraction guide (3a) and held in such a state by external means. Thus, the plunger subassembly (2a)-(2f), (3a)-(3d), (5) is prepared to be assembled with the barrel subassembly (1a)-(1d), (4a)-(4c), (6).

The plunger subassembly (2a)-(2f), (3a)-(3d), (5) is reciprocally received into the barrel subassembly (1a)-(1d), (4a)-(4c), (6) and inserted to a point where the insert (5) is snapped into place using radial concavities and convexities aligned on the radial surface of the insert (5) and the interior of the open end of the barrel (1a), respectively. Thus, the syringe is assembled in an embodiment represented by FIG. 9.

Referring to FIGS. 1, 7 and 8, FIG. 9 represents the syringe in its initial operational state, prepared for use with the plunger subassembly (2a)-(2f), (3a)-(3d), (5) rendered immovable in either axial direction by notches in the ribs of the plunger (1a) structure misaligned with the opening in the insert (5). The hollow needle (4a) is protected and caused to be contained using a cylindrical cover (6). The retraction system is in an armed condition resulting from the above-mentioned assembly process. The hypodermic syringe, according to the invention is put into service by removal of the protective cover (6) exposing the hollow needle (4a) and rotating the circular cap (3d) approximately 45 degrees or until the ribs of the plunger (1a) structure are caused to become aligned with a corresponding opening in the radial plane of the insert (5) allowing the plunger assembly (2a)-(2f), (3a)-(3d) to be adjusted axially. Thus, the syringe is prepared for loading. The loading of the syringe is commenced by inserting the hollow needle (4a) into an area or process to a point engaging a liquid source and pulling the plunger assembly (2a)-(2f), (3a)-(3d) by grasping the circular cap (3d) and pulling in one direction while concurrently pulling the barrel (1a) in an opposite direction, thereby adjusting the location of the plunger assembly (2a)-(2f), (3a)-(3d) within the barrel (1a). Thus, causing source liquid to be drawn through the hollow needle (4a) as a result of a vacuum caused by the increasing geometry of the cylindrical chamber formed by the interior surfaces of the barrel (1a) and the inserted end of the plunger assembly (2a)-(2f), (3a)-(3d). FIG. 10 serves to illustrate the loaded condition showing a plunger assembly 2a)-(2f), (3a)-(3d) adjusted to approximately 25% of full capacity. The syringe is now reinserted into a patient, area or process and an injection stroke is initiated by grasping the tabs (1d) with the index and middle finger straddled about the barrel (1a) body and applying pressure with the thumb of the same hand to the circular cap (3d). As the area in the cylindrical chamber containing liquid is caused to decrease the liquid is pressurized and escapes by communicating through the hollow needle and effectively into the patient, area or process so selected. As the plunger assembly (2a)-(2f), (3a)-(3d) approaches the end of the injection stroke a convex mating member extending from the retraction guide (3a) inserts and captures four mating members (4c) extending from the needle carriage (4b). Substantially toward the end of the injection stroke FIG. 11 an angled circular surface at the inserted or mating end of the plunger (2a) comes in contact with four latches (1c). As the injection stroke continues, the catches (1c) are caused to be deflected outward by angular forces being applied by the contacting surfaces of the plunger (2a). Raised surfaces previously restraining the needle carriage (4b) are cleared, thus, releasing the needle carriage subassembly (4a)-(4c). As the injection stroke finalizes, spherical bearings (2b) in locking contact with the retraction guide, (3a) align with a radial concave interior surface (1b) allowing force acting on the spherical bearings (2b) to transmit them outward and away from the centerline of the syringe and into the radial concave surface (1b). Thus releasing the retraction guide (3a) mated with the needle and carriage subassembly (4a)-(4c) to be retracted into the cylindrical cavity within the structure of the plunger (2a) by a biasing means or spring coming into mechanical equilibrium. Weep holes, (2e) in the cylindrical cavity of the plunger, (2a) facilitates evacuation of air trapped in the cavity as the retraction guide (3a) retreats into the cavity thereby displacing air into and out of the area between the barrel (1a) and the plunger (2a) body. Holes in the radial plane of the insert, (5) at the open end of the barrel, (1a) provide further relief of air both in the adjustment of the plunger assembly (2a)-(2f), (3a)-(3d) and the displacement of air by movement of the retraction guide (3a).

FIG. 12 illustrates the final state of the syringe according to the present invention. The contaminated hollow needle (4a) is caused to be contained within the cylindrical cavity and caused to be harmless, useless and safe for handling and transport to disposal means.

Figure 7:
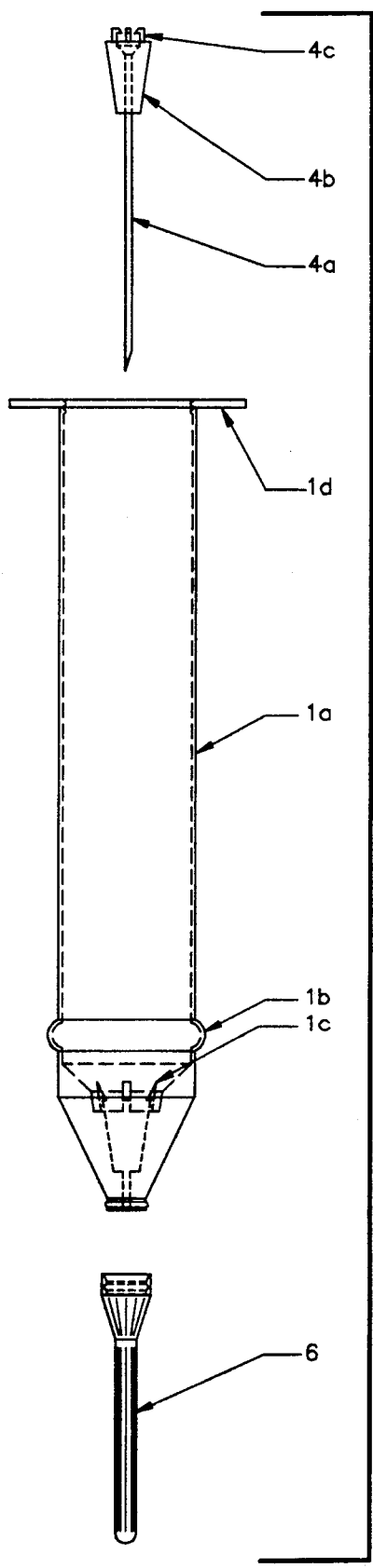
FIG. 7 is an exploded view of the barrel assembly parts in relative positions required for their assembly.

FIG. 13 illustrates a modified barrel (1a), (1b), (1d) whereby a portion of the cone shaped end of the modified barrel (1a), (1b), (1d) is previously detached creating a carriage bushing (7). The needle and carriage subassembly (4a)-(4c) and protective cover (6) are assembled to create a detached needle assembly (4a)-(4c), (6), (7). Radially concave and convex surfaces are employed at the forward interior cone shaped end of the modified barrel (1a), (1b), (1d) and at the exterior midsection of the carriage bushing (7) respectively, to subsequently restrain and create an airtight engagement between the needle assembly (4a)-(4c), (6), (7) and the modified barrel (1a), (1b), (1d). The modified barrel (1a), (1b), (1d) of FIG. 13 differs from the barrel (1a)-(1d) of FIG. 7 in that approximately one half of the cone shaped end of the barrel (1a)-(1d) of FIG. 7 is removed to form the substantial portion of the carriage bushing (7). In addition, the catches (1c) of FIG. 7 are now a feature of the carriage bushing (7).

FIG. 14 illustrates the major assembled parts of the hypodermic syringe in a condition immediately prior to FIG. 9 whereby options would be available in the selection of a needle subassembly (4a)-(4c), (6), (7) and hence an appropriate needle for a given application or usage.

While these embodiments of a hypodermic syringe as described herein are designed interrelatedly to themselves it will be understood the syringe is capable of adjustments and modifications to the system for ergonomic, economic, functional and aesthetic reasons. This application is, therefore, intended to specifically cover any variations, modifications, adjustments, uses or adaptations of the invention.

We claim hereupon:

1. A hypodermic safety syringe with a retracting needle system comprising;
    a transparent cylindrical body element for containing a liquid; having appurtenances interacting with;
    a previously detached needle assembly comprised of a bushing and a hollow needle temporarily interconnected with said bushing and body element for communicating liquid between said body element and a patient, area or process, said needle having a carriage and a hollow tine, said needle repositionable between an operable extreme wherein said needle projects axially outward from said body element and an inoperable extreme whereby said needle is retracted and contained completely within said body element; and a protective cover adapted to contain within, a portion of, said needle protruding from said barrel and further adapted to be detachably attached to said bushing and;
    a plunger reciprocally received into said body element whereby vacuum and pressurization forces are generated by adjustment of said plunger within said body element wherein liquid is drawn into said body element communicating through said needle by vacuum caused by adjusting said plunger outward from said body element and wherein liquid is expelled from said body element communicating through said needle by pressurization force caused by adjusting said plunger into said body element;
    a retraction mechanism whereby a retraction guide is permanently connected to a spring and in locking contact with spherical bearings thus held motionless within a cylindrical cavity within the plunger structure;
    a safing means associated with said hypodermic safety syringe with retracting needle system whereby the needle is automatically retracted into a cavity within said plunger substantially at the end of the injection stroke whereby mating members extending from the retraction guide and needle carriage engage and become captured as an angled surface on the plunger deflects latches restraining the needle and carriage assembly; spherical bearings within shafts in the plunger align with a radial concave interior surface of the barrel thereby releasing the retraction guide, captured needle and carriage assembly thereby retracting within the cavity in the plunger structure and rendering the syringe safe for handling and transport to disposal.

2. The hypodermic safety syringe of claim 1 wherein said needle and carriage assembly comprise a hollow needle permanently affixed within a tapered carriage with four radially aligned mating members adapted to receive, engage and capture an adapted mating member extending from a retraction guide armed within a plunger.

3. The hypodermic safety syringe of claim 2 wherein said plunger further consists of a front section containing latitudinal bores for receiving spherical bearings whereby a retraction guide is caused to be in locking contact with said bearings and restrained by force of a spring; said plunger further containing a cylindrical cavity adapted to receive said needle and carriage assembly upon retraction; this being facilitated by weep holes in the cylindrical cavity providing a means to exhaust air trapped within the cavity whereby said air is emitted into a space between the plunger and barrel.

4. The hypodermic safety syringe of claim 3 whereby said retraction guide having a protruding mating surface adapts to engage and capture said needle and carriage assembly; said retraction guide having radially concave surfacing thereby permitting said spherical bearings to encroach upon and render locked said retraction guide.

5. The hypodermic safety needle of claim 4 whereby said spring is permanently mated to said retraction guide and permanently mated to a circular cap affixed to the open end of the cylindrical cavity adapted to receive and restrain the circular cap; said spring providing a biasing means for restraining the retraction guide assisted through static position of said spherical bearings thereby providing a biasing means retracting the retraction guide and captured needle and carriage assembly automatically as the injection stroke achieves finality; Thereby rendering the syringe safe for handling and transport to disposal.

6. The hypodermic safety syringe of claim 5 whereby said plunger having longitudinal ribs with notches substantially adapted to fit snugly about an insert guide restrained at the open end of the barrel whereby said plunger can be caused to be rendered axially locked prior to and after use of said syringe.

7. The hypodermic safety syringe of claim 1 further comprising a graphic scale embossed upon the exterior surface of said barrel, accounting for internal volume losses and providing for measurability of volumes of liquid contained within the cylindrical chamber; said graphic scale units of measurement corresponding to particular industry requirements.

8. The hypodermic safety syringe of claim 1 whereby said cylindrical cavity is caused to contain a sufficient vacuum force acting on said retraction guide in a manner as a biasing means; thereby providing a force acting in conjunction with said spherical bearings whereby said retraction guide is locked motionless and automatically retracting the retraction guide and captured needle and carriage assembly as the injection stroke reaches finality; thereby rendering the syringe safe for handling and transport to disposal.

9. A hypodermic safety syringe with a retracting needle system comprising;
    a substantially transparent elongated tubular body having a conical end with an open bore adapted to receive and restrain a bushing, said tubular body having an opposite open end with opposing elliptical flanges at right angles with said tubular body, said tubular body interacting with;
    a bushing, through and about which, is attached, a needle and carriage subassembly comprising a carriage containing a permanently attached tubular hollow needle through which liquid or gas is communicated, said carriage adapted to become captured within said bushing and temporarily restrained into an air-tight engagement, said bushing being configured to receive and temporarily restrain a cover, within which, the remaining portion of said needle is reciprocally received to an extent said bushing comes in contact with and restrains said cover, therefore creating a needle assembly, interacting with;

a piston concentrically inserted into said tubular body and adapted to be in an air-tight engagement with said tubular body; the axial movement of said piston within said tubular body or the axial movement of said tubular body about said piston causing pressurization and vacuum forces alternately capable of communicating liquid or gas through said needle out of or into, respectively, said tubular body, interacting with;

a stored force, in the form of an extended spring attached to a retraction guide having adapted geometrical surfaces whereby ball bearings aligned at right angles on one or either side of said retraction guide and contained within hollow shafts are caused to be impaled against the interior surface of said tubular body, thus restraining the retraction guide at a predetermined axial position substantially at the inserted end of said piston, interacting with;

a disengaging means associated with said hypodermic safety syringe with retracting needle system, whereby said needle and carriage subassembly is caused to be repositioned into a hollow shaft within said piston containing the extended spring, substantially at the conclusion of the injection or pressurization stroke, whereby a protruding member at the forward end of said retraction guide engages and captures the pronged catches protruding from said needle carriage at which point additional forward movement engages the angular surfaces at the forward end of said piston against said latches protruding from said bushing; at substantially the end of the injection or pressurization stroke said latches are caused to be deflected radially outward sufficiently enough to release said needle and carriage subassembly, at which point, said ball bearings align with a radial concave groove, whereby said stored forces transmitted from said extended spring and surfaces of said retraction guide eject said ball bearing radially outward and into said radial groove to a point said retraction guide becomes unrestrained and yields to the forces of said spring, backward into said hollow shaft carrying with it said needle and carriage subassembly; whereby the syringe is devoid of a protruding needle and thereby safe for handling and transport to disposal.

10. The hypodermic safety syringe of claim 9 wherein said needle and carriage subassembly is comprised of a hollow tubular needle permanently attached partially within a conically tapered carriage adapted to be engaged and captured by means of four catch arms extending from the larger end of said carriage; by a mutually adapted mating member protruding from said retraction guide within the forward area of said piston.

11. The hypodermic safety syringe of claim 10 wherein said piston further contains hollow shafts at the forward section of said piston, adapted to receive and contain four ball bearings extending radially outward from the centerline of said piston; said bearings engaging an adapted surface of said retraction guide causing a temporary restraining of said retraction guide in a predetermined position; and further containing an axial hollow cylindrical shaft wherein is permanently affixed a spring and wherein said retraction guide, said needle and carriage subassembly and said spring are terminally housed in the final state of said hypodermic safety syringe; said hollow cylindrical shaft employing a means to allow venting of air as the internal volume is reduced by the reception of said retraction guide.

12. The hypodermic safety syringe of claim 11 whereby said retraction guide employs a forward protruding circular shaft having an adapted end surface capable of engaging and capturing the catch arms of said carriage; and further comprising surfaces about the midsection of said retraction guide adapted to interact in locking contact with said ball bearings; and further comprising an opposite end adapted to seat in air-tight contact with a surface at the forward end of said hollow cylindrical shaft and further adapted to attach said spring.

13. The hypodermic safety syringe of claim 12 whereby said spring is affixed within said hollow cylindrical shaft at one end to a cap snapped permanently into place in the opened end of said hollow cylindrical shaft and said spring affixed at the other end to said retraction guide; said spring providing a stored force acting in association with said retraction guide, said ball bearings, said needle and carriage subassembly as a means to relocate said members for the benefit of eliminating an exposed needle beyond said tubular body; thereby rendering the syringe safe for handling and transport to disposal.

14. The hypodermic safety syringe of claim 13 whereby said piston employs four longitudinal stiffening members having axially aligned cut outs provided to engage an insert snapped into permanent contact with flanged end of said tubular body, whereby said piston is momentarily restricted from axial motion before and after operation of said hypodermic safety syringe.

15. The hypodermic safety syringe of claim 14 further comprised of markings displayed on the exterior surface of said tubular body; said markings constituting accepted industry standards for visual reference of volumes contained in said hypodermic safety syringe.

* * * * *